(12) United States Patent
Schwarz et al.

(10) Patent No.: US 7,939,094 B2
(45) Date of Patent: *May 10, 2011

(54) MULTIPHASE POLYMERIC DRUG RELEASE REGION

(75) Inventors: Marlene C. Schwarz, Auburndale, MA (US); Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1027 days.

This patent is subject to a terminal disclaimer.

(21) Appl. No.: 10/175,526

(22) Filed: Jun. 19, 2002

(65) Prior Publication Data

US 2003/0235603 A1 Dec. 25, 2003

(51) Int. Cl.
*A61F 2/00* (2006.01)
*A61K 47/32* (2006.01)
*A61K 9/14* (2006.01)

(52) U.S. Cl. .......... 424/426; 514/772.4; 424/486
(58) Field of Classification Search .......... 424/426, 424/422, 423, 486; 514/772.4
See application file for complete search history.

(56) References Cited

U.S. PATENT DOCUMENTS

| | | | |
|---|---|---|---|
| 4,946,899 A | 8/1990 | Kennedy et al. | 525/244 |
| 5,258,020 A | 11/1993 | Froix | 623/1 |
| 5,304,121 A * | 4/1994 | Sahatjian | 604/509 |
| 5,616,608 A | 4/1997 | Kinsella et al. | 514/449 |
| 5,660,928 A * | 8/1997 | Stokes et al. | 428/32.25 |
| 5,716,981 A | 2/1998 | Hunter et al. | 514/449 |
| 5,733,925 A | 3/1998 | Kunz et al. | 514/449 |
| 5,741,331 A | 4/1998 | Pinchuk | 623/11 |
| 5,856,367 A | 1/1999 | Barrows et al. | 521/64 |
| 5,877,224 A * | 3/1999 | Brocchini et al. | 514/772.2 |

(Continued)

FOREIGN PATENT DOCUMENTS

| | | |
|---|---|---|
| EP | 0 756 853 A | 2/1997 |
| EP | 0 923 953 A | 6/1999 |
| WO | WO 91/16869 | * 11/1991 |

(Continued)

OTHER PUBLICATIONS

Elabd et al. ("Triblock copolymer ionomer membranes: Part I. Methanol and proton transport," in Journal of Membrane Science, vol. 217, Issues 1-2, 1 Jun. 2003, pp. 227-242).*
Puskas et al. ("The effect of hard and soft segment composition and molecular architecture on the morphology and mechanical properties of polystyrene—polyisobutylene thermoplastic elastomeric block copolymers," in European Polymer Journal, vol. 39, Issue 10, Oct. 2003, pp. 2041-2049).*
Bettini, Ruggero et al., "Solubility effects on drug transport through pH-sensitive, swelling-controlled release systems: Transport of theophylline and metoclopramide monohydrochloride", Journal of Controlled Release 37 (1995) pp. 105-111.*

(Continued)

*Primary Examiner* — Blessing M Fubara
(74) *Attorney, Agent, or Firm* — Mayer & Williams PC; David B. Bonham; Keum J. Park (57) ABSTRACT

A method is provided for modulating the rate of release of a therapeutic agent from a release region, which constitutes at least a portion of an implantable or insertable medical device and which controls the rate at which the therapeutic is released from the medical device. The method comprises: (a) providing a release region that comprises (i) a therapeutic agent and (ii) polymer composition comprising two or more immiscible phases; and (b) modulating the rate of release of the therapeutic agent by changing the volume that is occupied by at least one of the immiscible polymer phases relative to the total volume of the release region that is formed. The release region can be, for example, a carrier layer, which comprises the therapeutic agent, or a barrier layer, which is disposed over a region that contains the therapeutic agent. In preferred embodiments, the release region is formed by a process comprising: (a) providing a solution comprising (i) a solvent and (ii) the polymer composition; and (b) forming the release region from the solution by removing the solvent from the solution.

20 Claims, 3 Drawing Sheets

U.S. PATENT DOCUMENTS

| | | | |
|---|---|---|---|
| 5,879,697 A | 3/1999 | Ding et al. | 424/422 |
| 5,954,706 A | 9/1999 | Sahatjian | 604/509 |
| 6,099,562 A | 8/2000 | Ding et al. | 623/1.46 |
| 6,159,142 A | 12/2000 | Alt | 600/3 |
| 6,280,411 B1 | 8/2001 | Lennox | 604/103.05 |
| 6,335,029 B1 | 1/2002 | Kamath et al. | 424/423 |
| 6,368,658 B1 * | 4/2002 | Schwarz et al. | 427/2.15 |
| 6,545,097 B2 * | 4/2003 | Pinchuk et al. | 525/240 |
| 2002/0042645 A1 | 4/2002 | Shannon | 623/1.13 |
| 2002/0045706 A1 | 4/2002 | Houston et al. | 525/100 |
| 2002/0107330 A1 | 8/2002 | Pinchuk et al. | 525/242 |
| 2003/0059454 A1 * | 3/2003 | Barry et al. | 424/423 |
| 2003/0236513 A1 * | 12/2003 | Schwarz et al. | 604/890.1 |

FOREIGN PATENT DOCUMENTS

| | | |
|---|---|---|
| WO | WO 95 10989 A | 4/1995 |
| WO | WO 98 56312 A | 12/1998 |
| WO | WO 00 21584 A | 4/2000 |
| WO | WO 00 32255 A | 6/2000 |
| WO | WO 00 62830 A | 10/2000 |
| WO | WO 03 011250 A | 2/2003 |

OTHER PUBLICATIONS

James F. Beecher et al., "Morphology and Mechanical Behavior of Block Polymers," *Journal of Polymer Science*, Part C, No. 26 (1969), pp. 117-184.

Kohtaro Kimishima et al., "Control of Self-Assembled Structures in Binary Mixtures of A-B Diblock Copolymer and A-C Diblock Copolymer by Changing the Interaction between B and C Block Chains," *Macromolecules*, vol. 32 (1999), pp. 2585-2596.

Richard J. Spontak et al., "Phase Behavior of Ordered Diblock Copolymer Blends: Effect of Compositional Heterogeneity," *Macromolecules*, vol. 29 (1996), pp. 4494-4507.

Hong G. Jeon et al., "Microphase and Macrophase Transitions in Binary Blends of Diblock Copolymers," *Macromolecules*, vol. 32 (1999), pp. 1803-1808.

Immiscible Polymer Blends. http://www.psrc.usm.edu/macrog/iblend.htm. 1998.

L.H. Sperling, *Polymeric Multicomponent Materials: An Introduction*, New York, John Wiley & Sons, pp. 284-285, 1997.

* cited by examiner

MULTIPHASE POLYMERIC DRUG RELEASE REGION

FIELD OF THE INVENTION

The present invention relates to implantable or insertable medical devices for controlled delivery of one or more therapeutic agents.

BACKGROUND OF THE INVENTION

Numerous medical devices have been developed for the delivery of therapeutic agents to the body. The desired release profile for the therapeutic agent is dependent upon the particular treatment at hand, including the specific condition being treated/prevented, the specific site of administration, the specific therapeutic agent selected, and so forth.

In accordance with certain delivery strategies, a therapeutic agent is provided beneath a polymeric barrier region or within a polymeric carrier region that is associated with an implantable or insertable medical device. Once the medical device is placed at a desired location within a patient, the polymeric region regulates the release of the therapeutic agent from the medical device. Methods are therefore needed to manipulate the release properties of such polymeric regions.

SUMMARY OF THE INVENTION

The above and other needs of the prior art are met by the present invention, which is directed to novel methods for modulating the rate of release of a therapeutic agent from an implantable or insertable medical device.

In accordance with an embodiment of the invention, a method is provided for modulating the rate of release of a therapeutic agent from a release region that constitutes at least a portion of an implantable or insertable medical device and that controls the rate at which the therapeutic is released from the medical device. The method comprises: (a) providing a release region that comprises a therapeutic agent and polymer composition comprising two or more immiscible phases; and (b) modulating the rate of release of the therapeutic agent by changing the volume that is occupied by at least one of the immiscible polymer phases relative to the total volume of the release region that is formed. The release region can be, for example, a carrier layer, which comprises the therapeutic agent, or a barrier layer, which is disposed over a region that contains the therapeutic agent.

In some embodiments of the invention, at least one of the immiscible phases corresponds to a homopolymer.

In other embodiments, at least one of the immiscible phases corresponds to a copolymer, such as a random or alternating copolymer.

In still others, at least two of the immiscible phases are provided by a block or graft copolymer. If desired, a third immiscible phase can be provided by a homopolymer, random copolymer or alternating copolymer.

For example, in accordance with one particularly preferred embodiment, two immiscible phases are provided by a block copolymer comprising polystyrene and polyisobutylene blocks, and a third immiscible phase is formed from a random copolymer formed from styrene and maleic anhydride monomers. In this embodiment, the rate of release of the therapeutic agent is increased by decreasing the volume occupied by the block copolymer relative to the total volume of the polymeric release region and by increasing the volume occupied by the random copolymer relative to the total volume of the polymeric release region.

In preferred embodiments, the release region is formed by a process comprising: (a) providing a solution comprising (i) a solvent and (ii) the polymer composition; and (b) forming the release region from the solution by removing the solvent from the solution.

An advantage of the present invention is that it provides an effective method for controlling the release profile of a therapeutic agent from an implantable or insertable medical device.

These and other embodiments and advantages of the present invention will become immediately apparent to those of ordinary skill in the art upon review of the Detailed Description and Claims to follow.

DETAILED DESCRIPTION OF THE INVENTION

The present invention provides a method for modulating the rate of release of a therapeutic agent from an implantable or insertable medical device. The method relies on phase separation of immiscible polymer pairs due to thermodynamic interactions.

Solvent based techniques are generally preferred in which a solution is provided that comprises the following: (i) a solvent, (ii) a polymer composition that phase separates into two or more immiscible polymer phases upon solvent removal and (iii) optionally, a therapeutic agent. The solvent is subsequently removed from the solution to form a polymeric release region for the medical device.

In the method of the present invention, the rate of release of the therapeutic agent from the medical device is modulated by changing the volume that is occupied by at least one of the immiscible polymer phases within the polymeric release region, relative to the total volume of the polymeric release region. Phase separation of immiscible polymer pairs due to thermodynamic interactions is well documented in the literature. Contributing factors include but are not limited to the composition and the molecular weight of the polymer pairs.

Each immiscible polymer phase within the phase-separated compositions of the present invention occupies a fraction of the total volume of the polymeric release region of which it is a part. The volume of a selected immiscible polymer phase relative to the total volume of the release region can be increased, for example, by increasing the amount of the polymer that corresponds to the selected immiscible polymer phase relative to total amount of polymer in the release region, for instance, by increasing the number and/or length of the polymer chains associated with the selected immiscible polymer phase. Some specific examples follow.

In a first set of examples, a polymer composition with two immiscible phases can be provided by blending two immiscible polymers, for instance: (a) two immiscible homopolymers, (b) a homopolymer and a copolymer that is not miscible with the copolymer, but which by itself forms a single phase upon solvent removal (e.g., a random copolymer, an alternating copolymer or a single phase block copolymer, which is in contrast with a block copolymer having immiscible blocks that are sufficiently large to result in phase separation upon solvent removal), or (c) first and second immiscible copolymers, each forming a single immiscible phase upon solvent removal. Taking the blend of first and second immiscible homopolymers as an illustrative example, the relative volume of the phase corresponding to the first homopolymer can be increased by increasing the amount of the first homopolymer that is added to the blend relative to the second homopolymer. This can be implemented, for example, by (a) increasing the length (molecular weight), but not the number, of the first homopolymer molecules, (b) by increasing the number, but not the length of the first homopolymer molecules, or (c) by increasing both the length and number of the first homopolymer molecules.

In the above first set of examples, two separate polymers are employed in the polymer compositions, with each polymer forming its own immiscible polymer phase upon solvent removal. However, a single block copolymer having two (or more) immiscible blocks can also be used to create a polymer composition having two (or more) polymer phases, so long as the blocks are sufficiently long to result in phase separation. Using a diblock copolymer with two immiscible blocks as an illustrative example, the relative volume of a phase corresponding to the first block can be increased by increasing the length the first block within the block copolymer, relative to the second block.

Combinations of the above are also possible. As a specific example, it is possible to provide polymer release regions containing (a) two polymer phases corresponding to immiscible blocks of sufficient length within a block copolymer and (b) a third polymer phase corresponding to a separate immiscible homopolymer.

Polymers for use in accordance with the present invention can be selected from a wide range of polymers, which may be, for example, linear or branched, natural or synthetic, or crosslinked or uncrosslinked. The selected polymers are preferably processable using solvent-based processing techniques, exhibiting immiscibility between at least two phases upon solvent removal. Appropriate polymers can be selected from the following, among others: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; maleic anhydride polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as various blends and copolymers of all the above.

One example of a preferred polymer composition for use in connection with the present invention is the combination of a maleic anhydride copolymer with at least one additional polymer.

As used herein, a "maleic anhydride copolymer" is a polymer formed from two or more dissimilar monomers, at least one of which is maleic anhydride or a maleic anhydride derivative, for example, the free acid, salt, or partial ester form of maleic anhydride. Such copolymers may be, for example, random, alternating, graft or block copolymers.

Exemplary maleic anhydride copolymers include copolymers of (1) maleic anhydride monomer (which may be present, for example, in any of the above forms, including the anhydride, free acid, acid salt, and partial ester forms) with (2) at least one additional unsaturated monomer, examples of which include: (a) alkylene monomers, such as ethylene, propylene, butylenes (e.g., butylene, isobutylene), isoprene and octadecenes (e.g., 1-octadecene); (b) halogenated alkylene monomers (e.g., tetrafluoroethylene and chloroethylene); (c) vinyl monomers and derivatives, such as methyl vinyl ether, vinyl acetate, vinyl ethylene (butadiene), vinyl chloride, vinyl pyrrolidone, vinyl cyanide (acrylonitrile), vinyl alcohol and vinyl aromatics (e.g., styrene and styrene derivatives such as alpha-methyl styrene, ring-alkylated styrenes or ring-halogenated styrenes or other substituted styrenes where one or more substituents are present on the aromatic ring); and (d) acrylic acid monomers and derivatives, such as methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide.

More preferred maleic anhydride copolymers include the following: copolymers of styrene and maleic anhydride (e.g., Dylark 232 and Dylark 322, available from Nova Chemicals, which are random copolymers of styrene and maleic anhydride and contain 7 wt % and 14 wt % maleic anhydride, respectively), copolymers of styrene and maleic anhydride derivatives (e.g., an alternating polymer of styrene and the partial methyl ester of maleic anhydride, in which 10-15% of the anhydride has been converted to the half-ester form, available from Aldrich Chemical), isobutylene maleic anhydride copolymers (e.g., an alternating polymer of isobutylene and maleic anhydride, available from Aldrich Chemical), ethylene maleic anhydride copolymers, methyl vinyl ether maleic anhydride copolymers, vinyl acetate maleic anhydride copolymers, octadecene maleic anhydride copolymers, and butadiene maleic anhydride copolymers.

Exemplary polymers for use in combination with the above maleic anhydride copolymers include block copolymers comprising at least two polymeric blocks A and B. Examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule.

One specifically preferred group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block with the triblock therefore denoted as BAB). Where n=3 or more, these structures are commonly referred to as star-shaped block copolymers.

Further examples include branched block copolymers, for example, dendritic block copolymers (e.g., arborescent block copolymers) wherein at least one of the A and B chains is branched, and preferably wherein the A chains are branched and capped by the B chains.

The A blocks are preferably soft elastomeric components which are based upon one or more polyolefins or other polymer with a glass transition temperature at or below room temperature. For example, the A blocks can be polyolefinic blocks having alternating quaternary and secondary carbons of the general formulation: —(CRR'—(CH$_2$)$_n$—, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups. Preferred polyolefinic blocks include blocks of isobutylene, (i.e., polymers where R and R' are the same and are methyl groups). A can also be a silicone rubber block, an acrylate rubber block, and so forth.

The B blocks are preferably hard thermoplastic blocks with glass transition temperatures significantly higher than the elastomeric A block that, when combined with the soft A blocks, are capable of, inter alia, altering or adjusting the hardness of the resulting copolymer to achieve a desired combination of qualities. Preferred B blocks are polymers of methacrylates or polymers of vinyl aromatics. More preferred B blocks are (a) made from monomers of styrene styrene derivatives (e.g., α-methylstyrene, ring-alkylated styrenes or ring-halogenated styrenes) or mixtures of the same (collectively referred to herein as "styrenic blocks" or "polystyrenic blocks") or are (b) made from monomers of methylmethacrylate, ethylmethacrylate hydroxyethyl methacrylate or mixtures of the same.

In some particularly preferred embodiments of the present invention, a maleic anhydride copolymer, more preferably a styrene maleic anhydride copolymer, is combined with the following: (a) a copolymer of polyisobutylene with polystyrene or polymethylstyrene, more preferably polystyrene-polyisobutylene-polystyrene triblock copolymers that, along with other polymers appropriate for the practice of the present invention, are described, for example, in U.S. Pat. No. 5,741,331, U.S. Pat. No. 4,946,899 and U.S. Ser. No. 09/734,639, each of which is hereby incorporated by reference in its entirety; (b) arborescent polyisobutylene-polystyrene block copolymers such as those described in Kwon et al., "Arborescent Polyisobutylene-Polystyrene Block Copolymers-a New Class of Thermoplastic Elastomers," *Polymer Preprints,* 2002, 43(1), 266, the entire disclosure of which is incorporated by reference, or (c) a copolymer containing one or more blocks of polystyrene and one or more random polymer blocks of ethylene and butylene, for example, a polystyrene-polyethylene/butylene-polystyrene (SEBS) copolymer, available as Kraton® G series polymers. An additional preferred polymer for use in combination with the maleic anhydride copolymer is an n-butyl methacrylate (BMA) polymer available from Aldrich Chemical.

The release regions of the present invention can also include further auxiliary materials to achieve a desired result. Such auxiliary materials include binders, blending agents, and so forth.

Carrier layers and barrier layers are two preferred release regions for use in connection with the present invention. By "carrier layer" is meant a layer that contains at least one therapeutic agent and from which the therapeutic agent is released. By "barrier layer" is meant a layer that is provided between a therapeutic agent source and a site of intended release, which controls the rate of therapeutic agent release.

The release regions of the present invention are preferably formed using solvent-based techniques in which the polymers forming the release region are dissolved in a solvent.

The resulting solution is subsequently used to form the release region, for example, a carrier layer and/or barrier layer as desired.

The solvent system that is selected will contain one or more solvent species. The solvent system preferably is a good solvent for the polymers and, where included, for the therapeutic agent as well. The particular solvent species that make up the solvent system may also be selected based on other characteristics including drying rate and surface tension.

Solvent species that can be used in connection with the present invention include any combination of one or more of the following: (a) water, (b) alkanes such as ethane, hexane, octane, cyclohexane, heptane, isohexane, butane, pentane, isopentane, 2,2,4-trimethlypentane, nonane, decane, dodecane, hexadecane, eicosane, methylcyclohexane, cis-decahydronaphthalene and trans-decahydronaphthalene, (c) aromatic species such as benzene, toluene, xylene(s), naphthalene, styrene, ethylbenzene, 1-methylnaphthalene, 1,3,5-trimethylbenzene, tetrahydronaphthalene, diphenyl and 1,4-diethylbenzene, (d) halohydrocarbons including (i) chlorohyhdrocarbons such as chloroform, methyl chloride, dichloromethane, 1,1-dichloroethylene, ethylene dichloride, ethylidene chloride, propyl chloride, cyclohexyl chloride, 1,1,1-trichloroethane, perchloroethylene, trichloroethylene, butyl chloride, carbon tetrachloride, tetrachloroethylene, chlorobenzene, o-dichlorobenzene, benzyl chloride, trichlorobiphenyl, methylcyclohexane, 1,1,2,2-tetrachloroethane (ii) fluorinated halogenated species such as chlorodiflouoromethane, dichlorofluoromethane, dichlorodifluoromethane, trichlorofluoromethane, 1,2-dichlorotetrafluoroethane, 1,1,2-trichlorotrifluoroethane, perfluor(methylcyclohexane), perfluor(dimethylcyclohexane) and (iii) other halohydrocarbons such as ethyl bromide, ethylidene bromide, ethylene dibromide, tribromomethane, bromotrifluoromethane, 1,1,2,2-tetrabromoethane, bromobenzene, bromochloromethane, 1-bromonaphthalene, methyl iodide, methylene diiodide (e) acid aldehydes/anhydrides such as acetaldehyde, furfural, butyraldehyde, benzaldehyde, acetyl chloride, succinic anhydride and acetic anhydride, (f) alcohols including (i) phenols such as phenol, 1,3-benzenediol, m-cresol, o-methoxyphenol, methyl salicylate and nonylphenol, (ii) polyhydric alcohols such as ethylene glycol, glycerol, propylene glycol, 1,3-butanediol, diethylene glycol, triethylene glycol, hexylene glycol and dipropylene glycol, and (iii) other alcohols such as methanol, ethanol, ethylene cyanohydrin, allyl alcohol, 1-propanol, 2-propanol, 3-chloropropanol, furfuryl alcohol, 1-butanol, 2-butanol, benzyl alcohol, isobutanol, cyclohexanol, 1-pentanol, 2-ethyl-1-butanol, diacetone alcohol, 1,3-dimethyl-1-butanol, ethyl lactate, butyl lactate, ethylene glycol monomethyl ether, ethylene glycol monoethyl ether, diethylene glycol monomethyl ether, diethylene glycol monoethyl ether, ethylene glycol monobutyl ether, 2-ethyl-1-hexanol, 1-octanol, 2-octanol, diethylene glycol monobutyl ether, 1-decanol, 1-tridecyl alcohol, nonyl-phenoxy ethanol, oleyl alcohol, triethylene glycol mono-oleyl ether, (g) ethers such as, epichlorohydrin, furan, 1,4-dioxane, dimethoxymethane, diethyl ether, bis-(2-chloroethyl) ether, anisole, di-(2-methoxyethyl) ether, dibenzyl ether, di-(2-chloroisopropyl) ether, bis-(m-phenoxyphenol) ether, dimethyl ether and tetrahydrofuran, (h) ketones, such as acetone, cylohexanone, isophorone, diethyl ketone, mesityl oxide, acetophenone, methyl ethyl ketone, methyl isoamyl ketone, methyl isobutyl ketone, and methyl propyl ketone, (i) acids such as formic acid, acetic acid, benzoic acid, butyric acid, octanoic acid, oleic acid, stearic acid, (j) esters/acetates such as ethylene carbonate, butyrolactone, propylene-1,2-carbonate, ethyl chloroformate, ethyl acetate, trim- ethyl phosphate, diethyl carbonate, diethyl sulfate, ethyl formate, methyl acetate, n-butyl acetate, isobutyl acetate, t-butyl acetate, 2-ethoxyethyl acetate, isoamyl acetate, dimethyl phthalate, ethyl cinnamate, triethyl phosphate, diethyl phosphate, butyl benzyl phthalate, dibutyl phthalate, diethyl phthalate, tricrysyl phosphate, tributyl phosphate, dibutyl sebacate, methyl oleate, dioctyl phthalate, dibutyl stearate isopropyl acetate, isobutyl isobutyrate, n-propyl acetate and n-butyl propionate, (k) nitrogen compounds such as acetonitrile, acrylonitrile, propionitrile, butyronitrile, nitromethane, nitroethane, 2-nitropropane, nitrobenzene, ethanolamine, ethylenediamine, 1,1-dimethylhydrazine, 2-pyrrolidone, pyridine, propylamine, morpholine, analine, n-methyl-2-pyrrolidone, butylamine, diethylamine, cyclohexylamine, quinoline, dipropylamine, formamide, n,n-dimethylformamide, n,n-dimethylacetamide, tetramethylurea, hexamethyl phosphoramide, diethylenetriamine, triethylamine and triethanolamine, and (l) sulfur compounds such as carbon disulfide, dimethylsulfoxide, ethanethiol, dimethyl sulfone and diethyl sulfide.

Preferred solvent-based techniques include, but are not limited to, solvent casting, spin coating, web coating, solvent spraying, dipping, coating via air suspension and mechanical suspension techniques, ink jet techniques, electrostatic techniques, and combinations of these processes. Typically, a solution containing solvent and polymer (and, in some cases, a therapeutic agent) is applied to a substrate to form the release region. The substrate is preferably an implantable or insertable medical device, to which the release region is applied.

Where appropriate, techniques such as those listed above can be repeated or combined to build up the release region to a desired thickness. The thickness of the release region can be varied in other ways as well. For example, in one preferred process, solvent spraying, release region thickness can be increased by modification of the process parameters, including increasing spray flow rate, slowing the movement between the substrate to be coated and the spray nozzle, providing repeated passes and so forth.

Where a carrier layer is formed, a therapeutic agent can be included in the above-described polymer solution, if desired, and hence co-established with the carrier layer. Alternatively, the therapeutic agent can be dissolved or dispersed within a solvent, and the resulting solution contacted with a carrier layer that has been previously formed, for example, using one or more of the solvent based techniques described above (e.g., by dipping, spraying, etc.).

Barrier layers, on the other hand, are typically formed over a therapeutic-agent-containing region. In some embodiments, the therapeutic-agent-containing region beneath the barrier layer comprises one or more polymers, which can be selected, for example, from the polymers listed above. As such, the therapeutic-agent-containing region (which is, in essence, a carrier layer) can also be established using solvent-based techniques such as those discussed above (e.g., spraying, dipping, etc.).

In other embodiments, the therapeutic-agent-containing region beneath the barrier layer is established independent of an associated polymer. For example, the therapeutic agent can simply be dissolved or dispersed in a liquid, and the resulting solution/dispersion contacted with a substrate, for instance, using one or more of the above-described solvent based application techniques (e.g., by dipping, spraying).

Once a release region is formed using a solvent-based technique, it is preferably dried after application to remove the solvents. The release region typically conforms to the underlying surface during the drying process.

In accordance with the present invention, upon solvent removal, the release region comprises two or more immiscible polymer phases. As noted above, in the method of the present invention, the rate of release of the therapeutic agent from the medical device is modulated by changing the volume that is occupied by at least one of the immiscible polymer phases within the polymeric release region, relative to the total volume of the polymeric release region. Such volume changes are typically accompanied by changes in polymer phase morphology.

Using a diblock copolymer with two immiscible blocks as an illustrative example, the relative volume of a phase corresponding to the first block can be increased by increasing the length the first block within the block copolymer, relative to the second block. In many cases, a morphological progression like the following will be observed: (a) when the length of the first block is small relative to that of the second block, the first blocks forms small spherical domains within the release layer; (b) as the size of the first block is increased relative to that of the second block, the sizes of the spherical domains grow, in due course becoming cylindrical in shape; (c) a further increase in the size of the first block relative to that of the second block will result in the formation of a lamellar structure; (d) as the size of the first block continues to increase relative to that of the second block, cylindrical domains of the second block are formed, eventually becoming spherical domains. A similar domain transition is often observed in the case of two immiscible homopolymers. However, because the polymer chains are chemically bound to each other in the block copolymer, the homopolymer domains tend to be larger than the block copolymer domains. Of course, the above examples are merely illustrative and other domain morphologies are clearly possible.

Without wishing to be bound by theory, it is believed that morphological changes (which typically accompany a change in the volume occupied an immiscible polymer phase relative to the total volume of the polymeric release region) have an influence upon the diffusivity of a given therapeutic agent within the release layer. Returning again to the example of a release region having two immiscible phases, the diffusivity of a therapeutic agent within one of these phases is commonly significantly greater than it is within the other of these phases. As the relative volume occupied by the higher diffusivity phase is diminished relative to the lower diffusivity phase, the changes in morphology will result in the therapeutic agent traveling along an increasingly tortuous path, which decreases the overall diffusivity of the therapeutic agent within the release region.

Preferred implantable or insertable medical devices for use in conjunction with the present invention include catheters (for example, urinary catheters and vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including GDC—Guglilmi detachable coils—and metal coils), vascular grafts, myocardial plugs, patches, pacemakers and pacemaker leads, heart valves, biopsy devices or any coated substrate (which can be, for example, glasses, metals, polymers, ceramics and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the treatment of any mammalian tissue or organ. Non-limiting examples are tumors; organs including but not limited to the heart, coronary or peripheral vascular system, lungs, trachea, esophagus, brain, liver, kidney, bladder, urethra and ureters, eye, intestines, stomach, pancreas, ovary, and prostate; skeletal muscle; smooth muscle; breast; cartilage; and bone.

In some instances, it may be desirable to temporarily enclose the therapeutic-agent-loaded carrier layer to prevent initiation of release before the medical device reaches its ultimate placement site. As a specific example, a stent having a controlled release carrier layer can be covered with a sheath during insertion into the body to prevent premature release of therapeutic agent.

Therapeutic agents useful in connection with the present invention include essentially any therapeutic agent that is compatible with the release region selected and with the process used for forming the same. Therapeutic agents may be used singly or in combination.

"Therapeutic agents", "pharmaceutically active agents", "pharmaceutically active materials", "drugs" and other related terms may be used interchangeably herein and include genetic therapeutic agents, non-genetic therapeutic agents and cells.

Exemplary non-genetic therapeutic agents include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors of interest for delivery of genetic therapeutic agents include (a) plasmids, (b) viral vectors such as adenovirus, adenoassociated virus and lentivirus, and (c) non-viral vectors such as lipids, liposomes and cationic lipids.

Cells include cells of human origin (autologous or allogeneic), including stem cells, or cells from an animal source (xenogeneic), which can be genetically engineered if desired to deliver proteins of interest.

Numerous therapeutic agents, not necessarily exclusive of those listed above, have been identified as candidates for vascular treatment regimens, for example, as agents targeting restenosis. Such agents are appropriate for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β, pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs(6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents appropriate for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

The invention is further described with reference to the following non-limiting Examples.

Example 1

A solution is provided that contains 25 weight % tetrahydrofuran (THF) and 74 wt % toluene, 0.25 wt % paclitaxel and 0.75 wt % of a polymeric material, which consists of a polystyrene-polyisobutylene-polystyrene block copolymer (SIBS) or a random copolymer of styrene and maleic anhydride containing approximately 14 wt % maleic anhydride (SMA14), or a blend of these polymers. The SIBS copolymer is synthesized using known techniques such as those described in U.S. Pat. No. 5,741,331, U.S. Pat. No. 4,946,899 and U.S. Ser. No. 09/734,639. The SMA14 copolymer is purchased from Sigma-Aldrich, or is available from Nova Chemical as Dylark 332. All solutions are prepared by (1) mixing the paclitaxel and tetrahydrofuran, (2) adding the copolymer or copolymers, (3) adding the toluene, (4) thoroughly mixing (e.g., overnight), and (5) filtering.

The solution is then placed in a syringe pump and fed to a spray nozzle. A stent is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes.

After a carrier coating is formed in this fashion, the stent is dried, for example, by placing it in a preheated oven for 30 minutes at 65° C., followed by 3 hours at 70° C.

Three stents are formed in this manner for each of the various polymeric materials. Formulations were made containing (a) 0.75 wt % SMA14, (b) 0.5 wt % SMA14 and 0.25 wt % SIBS, (c) 0.3 wt % SMA14 and 0.45 wt % SIBS, (d) 0.2 wt % SMA14 and 0.55 wt % SIBS, (e) 0.15 wt % SMA14 and 0.60 wt % SIBS, (f) 0.1 wt % SMA14 and 0.65 wt % SIBS (two data sets), (g) 0.05 wt % SMA14 and 0.7 wt % SIBS, and (h) 0.75 wt % SIBS. For each formulation containing the styrene maleic anhydride copolymer, the polymer was added to the formulation at the same time as the polystyrene-polyisobutylene-polystyrene copolymer such that the total amount of polymer totaled 0.75% by weight of the formulation. The amount of paclitaxel remained constant at 0.25% by weight of the mixture, and the solvent combination (25 wt % THF and 74 wt % toluene) remained constant.

Paclitaxel release was then measured as a function of time in PBS with 0.5 wt % Tween® (polyoxyethylene(20) sorbitan monolaurate) available from Sigma-Aldrich. The results, presented as the cumulative release of paclitaxel as a function of time, are graphically illustrated in FIGS. 1A and 1B.

Figure 1A:
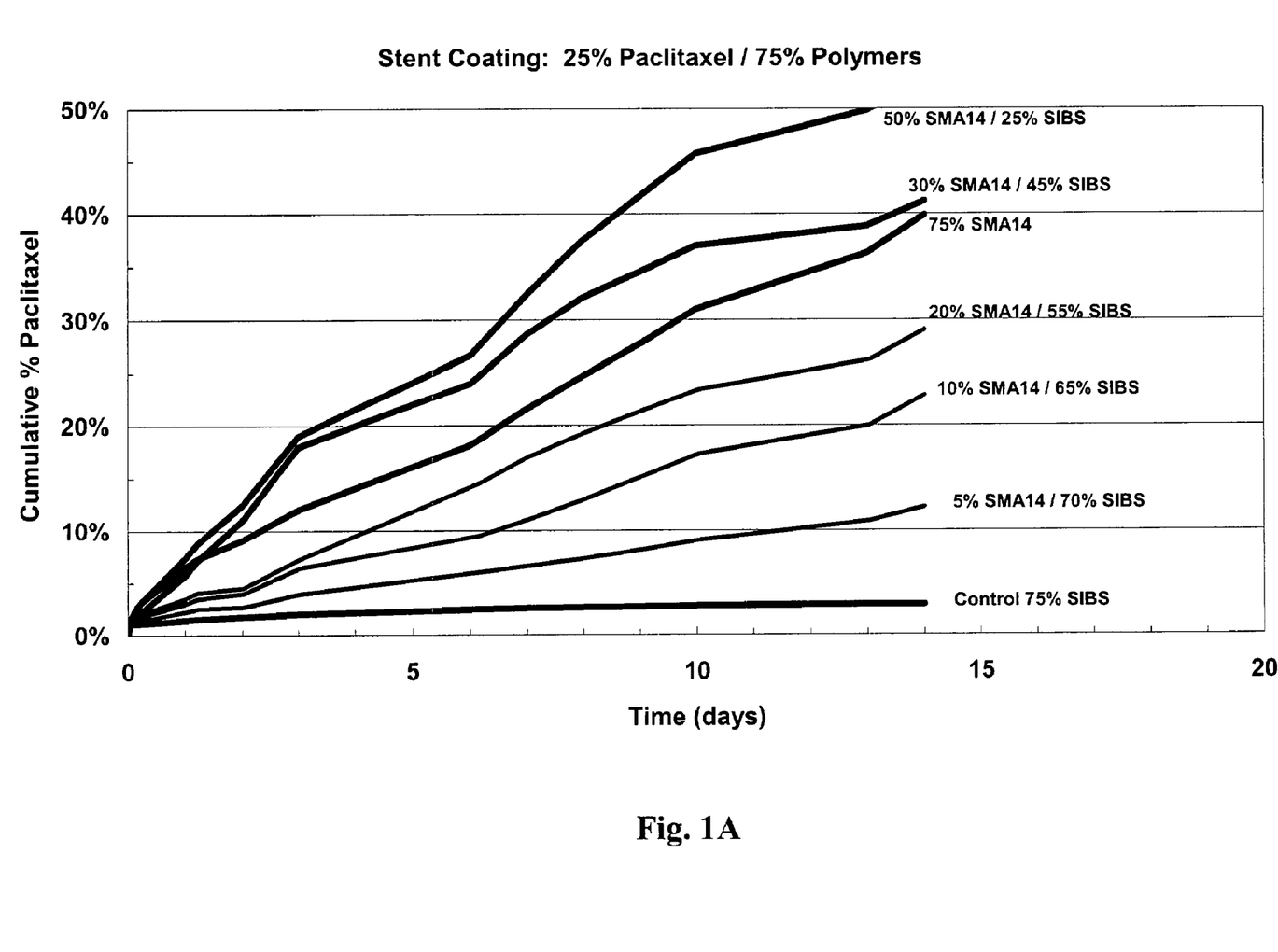
FIGS. 1A and 1B illustrate cumulative release of paclitaxel as a function of time for carrier layers containing (a) a polystyrene-polyisobutylene-polystyrene block copolymer, (b) a random copolymer of styrene and maleic anhydride, or (c) a polystyrene-polyisobutylene-polystyrene block copolymer blended with a random copolymer of styrene and maleic anhydride, in accordance with an embodiment of the present invention.
Figure 1B:
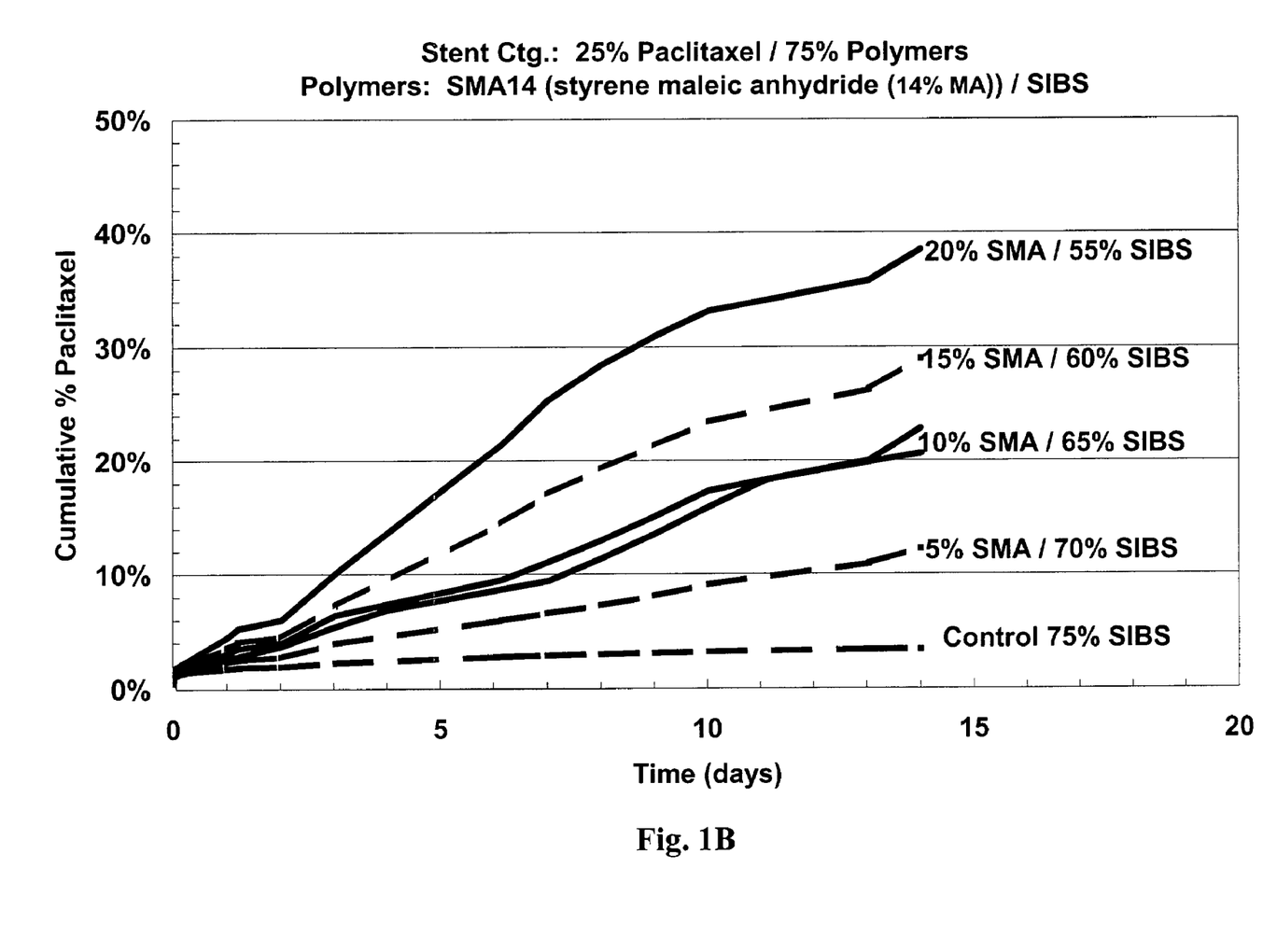

FIGS. 1A and 1B show that the release rate of paclitaxel from the SMA14 copolymer is relatively constant over time (sometimes referred to as "zero order" release). As the SIBS copolymer is added to the formulation it forms separate polymer phases that are immiscible with the initial SMA14 polymer phase. The size of the SMA14 polymer phase is reduced by the addition of the SIBS. As the amount of SIBS approaches greater than 50% the major phase becomes SIBS, and SMA14 is distributed within a SIBS matrix. As the amount of SIBS is further increased, the size of the SMA14 phase within the blend becomes smaller, and the rate of paclitaxel released from the coating is slowed.

Example 2

A solution is provided that contains the following: 5 wt % tetrahydrofuran (THF), 94 wt % toluene, 0.35 wt % paclitaxel and 0.65 wt % polystyrene-polyisobutylene-polystyrene block copolymer. The copolymer is synthesized using known techniques such as those described in U.S. Pat. No. 5,741,331, U.S. Pat. No. 4,946,899 and U.S. Ser. No. 09/734,639. The solution is provided by (1) mixing the paclitaxel and tetrahydrofuran, (2) adding the copolymer, (3) adding the toluene, (4) thoroughly mixing (e.g., overnight), and (5) filtering.

The solution is then placed in a syringe pump and fed to a spray nozzle. A stent is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes.

After a coating is formed in this fashion, it is dried, for example, by placing it in a preheated oven for 30 minutes at 65° C., followed by 3 hours at 70° C.

Nine stents are coated from the above formulation.

Two additional solutions are prepared containing the following: 25 wt % THF, 74 wt % toluene and 1 wt % of a polymer composition. One solution contains 1 wt % of SMA copolymer as described above. The second solution contains 0.5 wt % of SIBS and 0.5 wt % SMA14 (as described above).

Each of the solutions is individually placed in a syringe pump and fed to a spray nozzle. A coated stent (coated with the SIBS/paclitaxel formulation from above) is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes.

After a coating is formed in this fashion, it is dried, for example, by placing it in a preheated oven for 30 minutes at 65° C., followed by 3 hours at 70° C.

Three of the nine SIBS/paclitaxel coated stents are over coated with the 1.0% wt % SMA14 solution, and three of the SIBS/paclitaxel coated stents are over coated with the 0.50% SMA14 and 0.50% SIBS formulation, using the above procedure.

Figure 2:
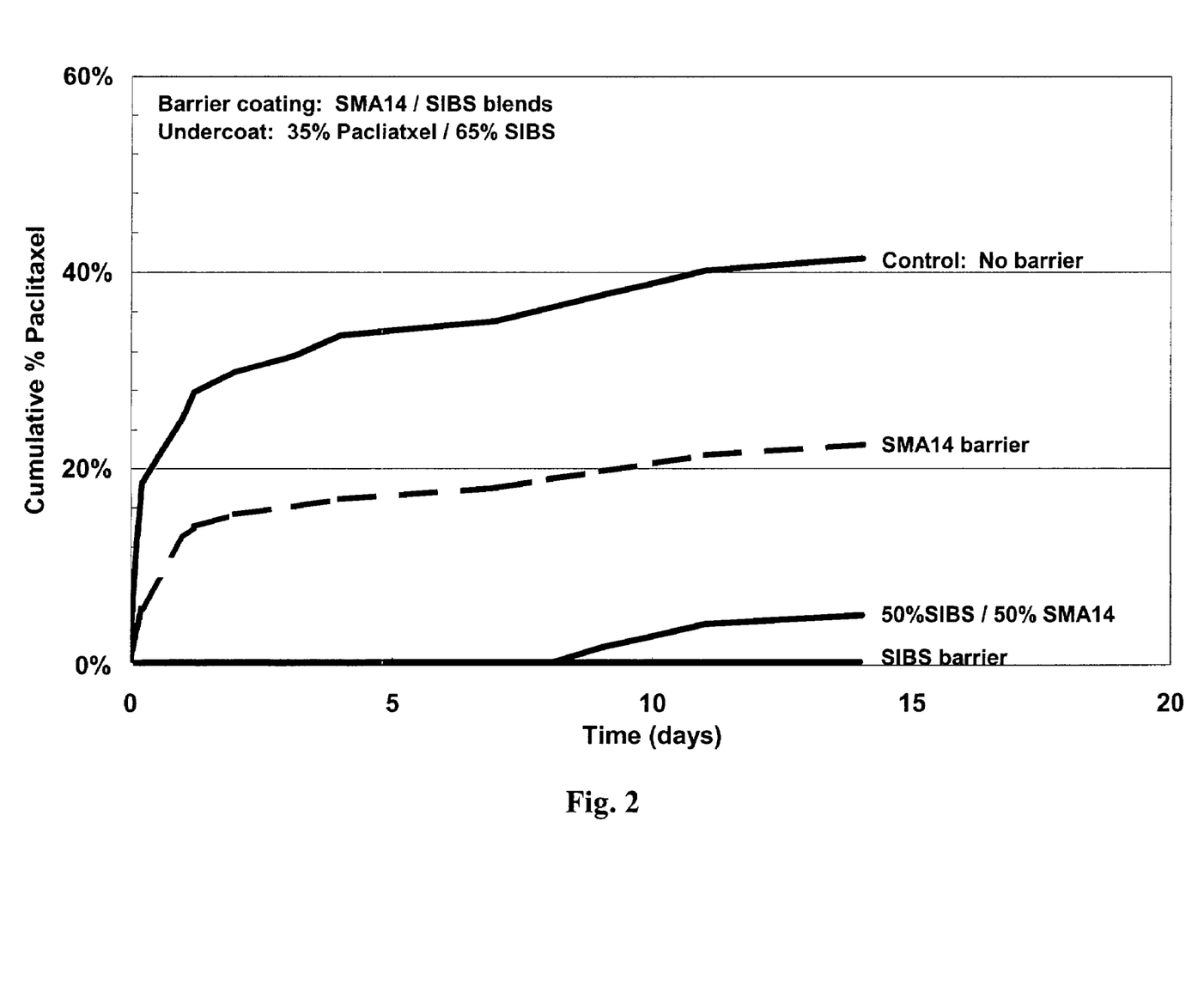
FIG. 2 illustrates cumulative release of paclitaxel as a function of time from barrier layers of (a) a random copolymer of styrene and maleic anhydride or (b) a combination of a random copolymer of styrene and maleic anhydride blended with a polystyrene-polyisobutylene-polystyrene block copolymer, in accordance with another embodiment of the present invention.

Cumulative release of paclitaxel as a function of time was then measured in PBS with 0.5% Tween® 20 (polyoxyethylene(20) sorbitan monolaurate) available from Sigma-Aldrich. The results are graphically illustrated in FIG. 2.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method for modulating a rate of release of a therapeutic agent from a release region that constitutes at least a portion of an implantable or insertable medical device and that controls the rate at which the therapeutic is released from the medical device, said method comprising:
    (a) providing a release region for said implantable or insertable medical device, said release region comprising a therapeutic agent and polymer composition that comprises three or more immiscible polymer phases, wherein at least two of said immiscible phases are provided by a block or graft copolymer and wherein at least one of said immiscible phases corresponds to an alternating or random maleic anhydride copolymer; and
    (b) modulating the therapeutic agent release rate characteristic of the release region by increasing the amount of the polymer that corresponds to at least one of the immiscible polymer phases relative to the total amount of polymer in the release region that is formed.

2. The method of claim 1, wherein said release region is a carrier layer.

3. The method of claim 1, wherein said release region is a barrier layer that is disposed over a region comprising said therapeutic agent.

4. The method of claim 1, wherein said release region is formed by a process comprising: (a) providing a solution comprising (i) a solvent and (ii) said polymer composition; and (b) forming said release region from said solution by removing said solvent from said solution.

5. The method of claim 4, wherein said release region is a carrier layer and wherein said solution further comprises said therapeutic agent.

6. The method of claim 4, wherein said release region is a carrier layer and wherein said therapeutic agent is provided within said carrier layer subsequent to solvent removal.

7. The method of claim 4, wherein said solvent comprises two or more solvent species.

8. The method of claim 4, wherein said release region is formed by applying said solution to said medical device.

9. The method of claim 8, wherein said solution is applied by spray coating.

10. The method of claim 8, wherein said solution is applied by dipping.

11. The method of claim 1, wherein said alternating or random maleic anhydride copolymer comprises (a) a maleic anhydride monomer and (b) at least one additional monomer selected from alkylene monomers, halogenated alkylene monomers, vinyl monomers and acrylic acid monomers.

12. The method of claim 1, wherein said alternating or random maleic anhydride copolymer comprises (a) a maleic anhydride monomer and (b) at least one additional monomer selected from ethylene, propylene, butylene, isobutylene, isoprene, butadiene, 1-octadecene, tetrafluoroethylene, chloroethylene, methyl vinyl ether, vinyl acetate, vinyl chloride, vinyl pyrrolidone, acrylonitrile, vinyl alcohol, styrene, alpha-methyl styrene, ring-alkylated styrene, ring-halogenated styrene, methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide.

13. The method of claim 1, wherein said alternating or random maleic anhydride copolymer comprises (a) maleic anhydride monomer and (b) styrene or methyl methacrylate.

14. A method for modulating a rate of release of a therapeutic agent from a release region that constitutes at least a portion of an implantable or insertable medical device and that controls the rate at which the therapeutic is released from the medical device, said method comprising:
(a) providing a release region for said implantable or insertable medical device, said release region comprising a therapeutic agent and polymer composition that comprises three or more immiscible polymer phases, wherein at least two of said immiscible phases are provided by a block copolymer that comprises (i) one or more blocks selected from vinyl aromatic blocks and methacrylate blocks and (ii) one or more polyolefin blocks, and wherein at least one of said immiscible phases corresponds to an alternating or random copolymer; and
(b) modulating the therapeutic agent release rate characteristic of the release region by increasing the amount of the polymer that corresponds to at least one of the immiscible polymer phases relative to the total amount of polymer in the release region that is formed.

15. The method of claim 14, wherein said alternating or random copolymer is a maleic anhydride copolymer.

16. The method of claim 15, wherein two immiscible phases are provided by a block copolymer comprising polystyrene and polyisobutylene blocks, and wherein a third immiscible phase is formed from a random copolymer formed from styrene and maleic anhydride monomers.

17. The method of claim 16, wherein the rate of release of the therapeutic agent is increased by decreasing the amount of said block copolymer relative to the total amount of polymer in the polymeric release region and by increasing the amount of said random copolymer relative to the total amount of polymer in the polymeric release region.

18. The method of claim 14, wherein said block copolymer comprises (i) one or more blocks comprising a monomer selected from styrene, α-methylstyrene, ring-alkylated styrene, ring-halogenated styrene, methyl methacrylate, ethyl methacrylate, and mixtures thereof and (ii) one or more polyolefin blocks comprising alternating quaternary and secondary carbons of the general formulation: —$(CRR'—CH_2)_n$—, where n is a positive whole number and R and R' are selected from methyl, ethyl, propyl, isopropyl, butyl, isobutyl, cyclohexane and cyclopentane.

19. The method of claim 14, wherein said block copolymer comprises (i) one or more blocks comprising a monomer selected from styrene and methyl methacrylate and (ii) one or more polyisobutylene blocks.

20. The method of claim 19, wherein said alternating or random maleic anhydride copolymer comprises (a) maleic anhydride monomer and (b) styrene or methyl methacrylate.

* * * * *